United States Patent
Worley et al.

(10) Patent No.: US 10,178,866 B2
(45) Date of Patent: Jan. 15, 2019

(54) N-HALAMINE CONTAINING FIBROUS COMPOSITIONS AND USES THEREOF

(71) Applicant: Auburn University, Auburn, AL (US)

(72) Inventors: Shelby D. Worley, Auburn, AL (US); Royall M. Broughton, Opelika, AL (US); Idris Cerkez, Auburn, AL (US); Buket Demir, Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 14/875,334

(22) Filed: Oct. 5, 2015

(65) Prior Publication Data

US 2016/0106098 A1 Apr. 21, 2016

Related U.S. Application Data

(60) Provisional application No. 62/066,655, filed on Oct. 21, 2014.

(51) Int. Cl.
*A01N 25/34* (2006.01)
*A01N 43/50* (2006.01)
(Continued)

(52) U.S. Cl.
CPC ............. *A01N 43/50* (2013.01); *A01N 25/34* (2013.01); *A61L 15/46* (2013.01); *D06M 13/352* (2013.01);
(Continued)

(58) Field of Classification Search
CPC ..... A01N 43/50; A01N 25/40; D06M 13/352; D06M 16/00; A61L 15/46; A61L 2420/02; A61L 2300/404; A61L 2300/204
See application file for complete search history.

(56) References Cited

U.S. PATENT DOCUMENTS 4,600,002 A 7/1986 Maryyanek et al.
4,969,457 A 11/1990 Hubbard et al.
(Continued)

FOREIGN PATENT DOCUMENTS

WO WO-02/03899 1/2002
WO WO-2004/087226 10/2004
(Continued)

OTHER PUBLICATIONS

A review on wound dressings with an emphasis on electrospun nanofibrous polymeric bandages: retrieved from internet: http://onlinelibrary.wiley.com/doi/10.1002/pat.1625/abstract. Retrived on Sep. 8, 2015.*

(Continued)

*Primary Examiner* — Hong Yu
(74) *Attorney, Agent, or Firm* — Barnes & Thornburg LLP (57) ABSTRACT

The present disclosure provides fibrous composition comprising a soluble or a dispersible N-halamine, for example 1-chloro-2,2,5,5-tetramethyl-4-imidazolidinone (i.e., compound I). Additionally, the disclosure provides methods for producing the fibrous compositions comprising a soluble or a dispersible N-halamine as well as methods for protecting a person from an infection using the fibrous compositions comprising a soluble or a dispersible N-halamine. The compositions and methods according to the present disclosure provide several advantages, such as stability, less time to provide sufficient antimicrobial inactivation, and are inexpensive and require lower amount of active concentrations to be effective.

14 Claims, 1 Drawing Sheet

(51) Int. Cl.
| | |
|---|---|
| A01N 59/16 | (2006.01) |
| A01N 59/20 | (2006.01) |
| A61L 15/46 | (2006.01) |
| D06M 16/00 | (2006.01) |
| D06M 23/10 | (2006.01) |
| D06M 13/352 | (2006.01) |

(52) U.S. Cl.
CPC ............ *D06M 16/00* (2013.01); *D06M 23/10* (2013.01); *A61L 2300/204* (2013.01); *A61L 2300/404* (2013.01); *A61L 2420/02* (2013.01)

(56) References Cited

U.S. PATENT DOCUMENTS

| | | | |
|---|---|---|---|
| 5,057,612 | A | 10/1991 | Worley et al. |
| 5,126,057 | A | 6/1992 | Worley et al. |
| 5,490,983 | A | 2/1996 | Worley et al. |
| 5,620,527 | A * | 4/1997 | Kramer ................. A01N 59/00 |
| | | | 134/2 |
| 6,681,765 | B2 | 1/2004 | Wen |
| 6,768,009 | B1 | 7/2004 | Sun et al. |
| 6,823,530 | B2 | 11/2004 | Quincy, III |
| 7,044,993 | B1 | 5/2006 | Bolduc |
| 7,520,923 | B2 | 4/2009 | Marcoon |
| 8,304,454 | B2 | 11/2012 | Truong |
| 8,764,851 | B2 | 7/2014 | Ghosh et al. |
| 8,883,077 | B2 | 11/2014 | Worley et al. |
| 2004/0191315 | A1 | 9/2004 | Slattery et al. |
| 2006/0275349 | A1 | 12/2006 | Andrews et al. |
| 2007/0048358 | A1 | 3/2007 | Schorr et al. |
| 2008/0229929 | A1 | 9/2008 | Marcoon |
| 2010/0272783 | A1 | 10/2010 | Wang et al. |
| 2011/0190392 | A1* | 8/2011 | Najafi ..................... A01N 41/08 |
| | | | 514/517 |
| 2016/0058008 | A1* | 3/2016 | Cao ...................... A01K 1/0152 |
| | | | 424/405 |

FOREIGN PATENT DOCUMENTS

| | | |
|---|---|---|
| WO | WO-2006/086271 | 8/2006 |
| WO | WO2008156636 A1 | 12/2008 |
| WO | WO-2011/107781 | 9/2011 |

OTHER PUBLICATIONS

Volatile Solvents: retrieved from internet: http://www.merckmanuals.com/professional/special-subjects/recreational-drugs-and-intoxicants/volatile-solvents. Retrieved on Sep. 8, 2016.*

Allam, O.G., "Improving Functional Characteristics of Wool and Some Synthetic Fibres," Open Journal of Organic Polymer Materials, 2011, 3, 8-19.

Borkow, G.; Zhou, S. S.; Page, T.; Gabbay, J. A., "Novel Anti-Influenza Copper Oxide Containing Respiratory Face Mask," *PloS One* 2010, 5(6), el 1295. DOI:1 0.1371/journal.pone.0011295.

Bosch, A. A. T. M.; Biesbroek, G.; Trzcinski, K.; Sanders, E. A. M.; Bogaert, D., "Viral and Bacterial Interactions in the Upper Respiratory Tract," *PLoS Pathog*. 2013, 9 (1), el003057. DOI: 10.1371/journal.ppat. 1003057.

Burke, J. P., "Infection Control—A Problem for Patient Safety," *N. Engl. ./. Med*. 2003, 348, 651-656.

Cao, Z.; Sun, X.; Sun, Y.; Fong, H., " Rechargeable Antibacterial and Antifungal Polymeric Silver Sulfadiazines," *J. Bioact. Compat. Polym*. 2009, 24 (4), 350-367.

CDC. "Interim Guidance for Protection of Persons Involved in U.S. Avian Influenza Outbreak Disease Control and Eradication Activities," *Department of Health and Human Services, Centers for Disease Control and Prevention*, Atlanta, Georgia, Jan. 2006.

Cerkez, I.; Worley, S. D.; Broughton, R. M.; Huang, T. S.. "Antimicrobial Surface Coatings for Polypropylene Nonwoven Fabrics," *React. Funct. Polym*. 2013, 73, 1412-1419.

Christian, J., "4-Imidazolidinethiones," 1957, J. Org. Chem., 22, 396-399.

Cozad, A.; Jones, R. D., "Disinfection and the Prevention of Infectious Disease," *Am. J. Infect. Control* 2003, 31, 243-254.

Dawood, F. S.; Jain, S.; Finelli, L.; Shaw, M. W.; Lindstorm, S.; Garten, R. J.; Gubareva, L. V.; Xu, X.; Bridges, C. B.; Uyeki, T. M., "Emergence of a Novel Swine-Origin Influenza a (H1N1) Virus in Humans," *N. Engl. J. Med*. 2009, 360, 2605-2615.

Demir et al., "N-halamine-Modified Antimicrobial Polypropylene Nonwoven Fabrics for Use against Airborne Bacteria," ACS Appl. Mat. Interf., 2015, 7, 1752-1757.

Hans, M.; Erbe, A.; Mathews, S.; Chen, Y.; Solioz, M.; Mucklich, F., "Role of Copper Oxides in Contact Killing of Bacteria," *Langmuir* 2013, 29, 16160-16166.

Hota, B., "Contamination, Disinfection, and Cross-Colonization: Are Hospital Surfaces Reservoirs for Nosocomial Infection?", *Clin. Infect. Dis*. 2004, 39, 1182-1189.

Hui, F.; Debiemme-Chouvy, C., "Antimicrobial N-Halamine Polymers and Coatings: A Review of Their Synthesis, Characterization, and Applications," *Biomacromolecules* 2013, 14, 585-601.

Jung, J. EL; Hwang, G. B.; Lee, J. E.; Bae, G. N., "Preparation of Airborne Ag/CNT Hybrid Nanoparticles Using an Aerosol Process and Their Application to Antimicrobial Air Filtration," *Langmuir* 2011, 27, 10256-10264.

Kenawy, E-R.; Worley, S. D.; Broughton, R. M., "The Chemistry and Applications of Antimicrobial Polymers: A State of the Art Review," *Biomacromolecules* 2007 8 (5), 1359-1384.

King, A.; Chakrabarty, S.; Zhang, W.; Zheng, X.; Ohman, D. E.; Wood, L. F.; Abraham, S.; Rao, R.; Wynne, K. J., "High Antimicrobial Effectiveness with Low Hemolytic and Cytotoxic Activity for PEG/Quaternary Copolyoxetanes," *Biomacromolecules* 2014, 15 (2), 456-467.

Lee, D. H.; Jung, J. H.; Lee, B. U., "Effect of Treatment with a Natural Extract of *Mukdenia Rossii* (*Oliv*) *Koidz* and Unipolar Ion Emission on the Antibacterial Performance of Air Filters," *Aerosol Air Qual Res*. 2013, 13, 771-776.

Lee, S. et al., "Developing protective textile materials as barriers to liquid penetration using melt-electrospinning," 2006, J. Appl. Polym. Sci., 102, 3430-3437.

Luo, J.; Porteous, N.; Sun, Y., "Rechargeable Biofilm-Controlling Tubing Materials for Use in Dental Unit Water Lines," *ACS Appl. Mater. Interfaces* 2011, 3 (8), 2895-2903.

Madkour, A. E.; Dabkowski, J. M.; Nusslein, K.; Tew, G. N., "Fast Disinfecting Antimicrobial Surfaces," *Langmuir* 2009; 25 (2), 1060-1067.

Marambio-Jones, C.; Hoek, E. M. V., "A Review of the Antibacterial Effects of Silver Nanomaterials and Potential Implications for Human Health and the Environment," *J. Nanopart. Res*. 2010, 12 (5), 1531-1551.

Martinez, J. L.; Baquero, F., "Interactions among Strategies Associated with Bacterial Infection: Pathogenicity, Epidemicity, and Antibiotic Resistance," *Clin. Microbiol. Rev*. 2002,15 (4), 647-679.

Paladini, F.; Cooper, I. R.; Pollini, M., "Development of Antibacterial and Antifungal Silver-Coated Polyurethane Foams as Air Filtration Units for the Prevention of Respiratory Diseases," *J. Appl. Microbiol*. 2013, 116, 710-717.

Palermo, E. F.; Kuroda, K., "Structural Determinants of Antimicrobial Activity in Polymers which Mimic Host Defense Peptides," *Appl. Microbiol. Biotechnol*. 2010, 57, 1605-1615.

Ren, G.; Hu, D.; Cheng, E. W. C.; Vargas-Reus, M. A.; Reip, P.; Allaker, R. P., "Characterisation of Copper Oxide Nanoparticles for Antimicrobial Applications," *Int. J. Antimicrob. Agents* 2009, 33 (6), 587-590.

Rengasamy, S.; Fisher, E.; Shaffer, R. E., "Evaluation of the Survivability of MS2 Viral Aerosols Deposited on Filtering Face Piece Respirator Samples Incorporating Antimicrobial Technologies," *Am. J. Infect. Control* 2010, 38, 9-17.

Sauvet, G.; Dupond, S.; Kazmierski, K.; Chojnowski, J., "Biocidal Polymers Active by Contact. V. Synthesis of Polysiloxanes with Biocidal Activity." *J. Appl. Polym. Sci*. 2000, 75, 1005-1012.

(56) References Cited

OTHER PUBLICATIONS

Sun, Y.; Sun, G., "Novel Refreshable N-halamine Polymeric Biocides: Grafting Hydantoin-Containing Monomers onto High Performance Fibers by a Continuous Process," *J. Appl. Polym. Sci.* 2003, 88, 1032-1039.

Sun, Y.; Sun, G., "Novel Regenerable N-halamine Polymeric Biocides. II. Grafting Hydantoin-Containing Monomers onto Cotton Cellulose," *J. Appl. Polym. Sci.* 2001, 81 (3), 617-624.

Tiliket, G.; Le Sage, D.; Moules, V.; Rosa-Calatrava, M.; Lina, B.; Valleton, J. M.; Nguyen, Q. T.; Lebrun, L., "A New Material for Airborne Virus Filtration," *Chem. Eng. J.* 2011, 173, 341-351.

Tsao, T.; Williams, D. E.; Worley, C. G.; Worley, S. D., "Novel N-Halamine Disinfectant Compounds," *Biotechnol. Prog.* 1991, 7(1), 60-66.

Wang, D.; Xu, W.; Sun, G.; Chiou, B., "Radical Graft Polymerization of an Allyl Monomer onto Hydrophilic Polymers and Their Antibacterial Nanofibrous membranes," *ACS Appl. Mater. Interfaces* 2011, 3, 2838-2844.

Willeke, K.; Qian, Y.; Donnelly, J.; Grinshpun, S.; Ulevicius, V., "Penetration of Airborne Microorganisms through a Surgical Mask and a Dust/Mist Respirator," *Am. Ind. Hyg. Assoc. J.* 1996, 57, 348-55.

Worley, S. D., et al., "Halamine Water Disinfectants," 1998, Crit. Rev. Environ. Sci. Technol, 18 (2), 133-175.

Worley, S. D.; Chen, Y.; Wang, J-W.; Wu, R.; Cho, U.; Broughton, R. M.; Kim, J.; Wei, C-; Williams, J. F.; Chen, J.; Li, Y. "Novel N-Halamine Siloxane Monomers and Polymers for Preparing Biocidal Coatings," *Surf. Coat. Int., Part B* 2005, 88, 93-100.

Xu, Z.; Yao, M., "Effects of Single-Walled Carbon Nanotube Filter on Culturability and Diversity of Environmental Bioaerosols," *J. Aerosol Sci.* 2011, 42, 387-396.

Yoon, K. Y.; Byeon, J. H.; Park, C. H.; Hwang, J., "Antimicrobial Effect of Silver Particles on Bacterial Contamination of Activated Carbon Fibers," *Environ. Sci. Technol*. 2008, 42, 1251-1255.
Zhu, J.; Bahramian, Q.; Gibson, P.; Schreuder-Gibson, H.; Sun G., "Chemical and Biological Decontamination Functions of Nanofibrous Membranes," *J. Mater. Chem*. 2012, 22, 8532-8540.
International Search Report and Written Opinion prepared for PCT/US2015/053989, dated Mar. 8, 2016, 11 pages.
Lei, Q. et al., "Durable and regenerable antimicrobial textiles: Synthesis and applications of 3-methylol-2,2,5,5-imidazolidin-4-one (MTMIO)," Journal of Applied Polymer Science, 2003, 89, 2418-2425.
Gang et al, "Chemistry of durable and regenerable biocidal textiles," Journal of Chemical Education, 2005, 82(1):60.

* cited by examiner

N-HALAMINE CONTAINING FIBROUS COMPOSITIONS AND USES THEREOF

CROSS-REFERENCE TO RELATED APPLICATIONS

This application claims the benefit under 35 U.S.C. § 119(e) of U.S. Provisional Application Ser. No. 62/066,655, filed on Oct. 21, 2014, the entire disclosure of which is incorporated herein by reference.

TECHNICAL FIELD

The invention relates to the incorporation of a stable, noncorrosive N-halamine compound in fibrous compositions such as, but not limited to air filters, facial masks, surgical materials, wound dressings, and wipes for use as infection prevention and for purposes of disinfection. The invention includes the fibrous compositions, methods of using the fibrous compositions, and methods of producing the fibrous compositions.

BACKGROUND AND SUMMARY OF THE INVENTION

For consistent improvement in the health care field, a continual search for novel antimicrobial compounds is highly desired. For example, a class of compounds known as organic N-halamines, which are generally heterocyclic monomers or polymers containing nitrogen-halogen bonds, can be evaluated. The most stable of these compounds with regard to the release of corrosive halogen in aqueous solution are those containing N—Cl covalent bonds stabilized by electron-donating substituents (e.g., alkyl groups such as methyl groups) attached to the carbon atoms in the cyclic structures directly linked to the nitrogen atom containing the oxidative halogen atom. The mechanism by which these stable N-halamine compounds inactivate pathogenic microorganisms is through a direct contact in which the N-halamine donates its halogen atom to the microbial cell, wherein the cell is inactivated through an oxidation process. If the N—Cl bond on the N-chloramine is sufficiently strong, the disinfection process will be slower than for "free chlorine," which is the antibacterial agent present in household bleach. However, if free chlorine is not appreciably released from an N-chloramine into aqueous media, then chemical processes such as corrosion and bleaching will desirably be minimized while, at the same time, maintaining antimicrobial activity.

Furthermore, a disposable fibrous matrix for use in inactivation of pathogens and other undesirable microorganisms upon direct contact is highly desired. In this regard, compositions utilizing silver nanoparticles and carbon nanotubes as antimicrobial agents have been explored, demonstrating a bacterial reduction after a 1200 minute residence time against *Staphylococcus epidermidis* and *Escherichia coli*. After the lengthy residence time, the relative bacterial viability was determined as 32%, 13%, 5%, and 0.9% on the control, carbon nanotube, silver nanoparticle, and silver/carbon nanotube modified filters, respectively, for *S. epidermidis*. Likewise, the relative bacterial viability was determined to be 13%, 2.1%, 0.4%, and 0.1% on the control, carbon nanotube, silver nanoparticle, and silver/carbon nanotube modified filters, respectively, for *E. coli*. Furthermore, complete inhibition of *E. coli* has been shown on silver-deposited activated carbon filters at a contact time of 60 minutes, and the necessary contact time for a complete inhibition of *Bacillus subtilis* was shown to be 10 minutes.

Another hurdle in the preparation of fibrous compositions is the desirable air penetration of materials, for example filter materials. Importantly, antimicrobial activity may be compromised if air penetration is reduced considerably by the process in which fibrous compositions are coated with antimicrobial compounds. Furthermore, an effective antimicrobial compound suspended in a wound dressing should ideally accentuate healing and prevent infections for patients inflicted with wounds. Although there are existing commercial products claiming to be effective for these purposes, such as those containing silver salts, quaternary ammonium salts, and biguanides, the existing products have numerous undesirable characteristics. For example, silver salts are expensive, and high concentrations are required to be effective. A typical silver concentration for an Aquacel® Silver Ag Dressing is 1.2% (w/w), and the cost varies from about $6 to $50 per bandage depending on size and use. Likewise, quaternary ammonium salts and biguanides are also expensive and can be less effective in inactivation rate, typically requiring over one hour to provide a 6-log inactivation of bacteria. Moreover, since microorganisms also cause undesirable odors, antimicrobial compounds suspended in a disposable fibrous matrix that are useful as an odor preventative are also highly desirable.

Therefore, there exists a need for a stable, inexpensive antimicrobial compound which can be suspended in a disposable fibrous matrix for use in the inactivation of pathogens and other undesirable microorganisms upon direct contact. Such an antimicrobial fibrous composition could find use in numerous disposable textile products, for example as air filters, facial masks, surgical materials, wound dressings, and wipes, in order to protect people from infections in their daily lives. Moreover, such antimicrobial fibrous compositions could be used in cartridges or pleated sheets in air-handling systems in airplanes, medical facilities, or even homes to prevent the spread of infections in the facilities. A highly desired application is for facial masks to protect medical personnel when such persons are in contact with infected patients and to protect the patients from nosocomial infections due to contact with the medical personnel.

Accordingly, the present disclosure provides fibrous compositions comprising one or more antimicrobial N-halamine compounds that exhibit desirable properties and provide related advantages for improvement in the health care field. The fibrous compositions and methods according to the present disclosure provide several advantages compared to those known in the art. First, N-halamine compounds are stable, inexpensive antimicrobial compounds which can be suspended in numerous fibrous compositions for utilization in many different applications. Second, the fibrous compositions comprising an N-halamine compound desirably require less time to provide sufficient antimicrobial inactivation. Third, the fibrous compositions comprising an N-halamine compound allow for ample air penetration of materials as a result of their preparation and can desirably accentuate healing and prevent infections when applied to patients with wounds. Fourth, the fibrous compositions comprising an N-halamine compound are inexpensive and require a lower amount of active concentration to be effective. Fifth, since microorganisms also cause undesirable odors, the fibrous compositions comprising an N-halamine compound can also be useful as odor preventative agents. Finally, since N-halamine compounds are mild oxidizing agents, compositions comprising an N-halamine compound are capable of oxidizing such toxic chemicals as the chemical warfare agent bis-dichloroethyl sulfide ("mustard").

The following numbered embodiments are contemplated and are non-limiting:

1. A fibrous composition comprising an N-halamine.
2. The fibrous composition of clause 1 wherein the N-halamine is a soluble N-halamine.
3. The fibrous composition of clause 1 wherein the N-halamine is a dispersible N-halamine.
4. The fibrous composition of any of clauses 1 to 3 wherein the N-halamine is selected from the group consisting of 1-chloro-2,2,5,5-tetramethyl-4-imidazolidinone, 3-chloro-4,4-dimethyl-2-oxazolidinone, 1,3-dichloro-2,2,5,5-tetramethyl-4-imidazolidinone, 1,3-dichloro-4,4,5,5-tetramethyl-2-imidazolidinone, tetrachloroglycoluril, and 1-chloro-2,2,6,6-tetramethyl-4-piperidinol.
5. The fibrous composition of any of clauses 1 to 3 wherein the N-halamine is 1-chloro-2,2,5,5-tetramethyl-4-imidazolidinone.
6. The fibrous composition of any of clauses 1 to 5 wherein the fibrous composition is a disposable fibrous composition.
7. The fibrous composition of any one of clauses 1 to 6 wherein the fibrous composition is a stable fibrous composition.
8. The fibrous composition of any of clauses 1 to 7 wherein the fibrous composition has a basis weight value of about 15 $g/m^2$ to about 25 $g/m^2$.
9. The fibrous composition of any of clauses 1 to 7 wherein the fibrous composition has a basis weight value of about 20 $g/m^2$ to about 50 $g/m^2$.
10. The fibrous composition of any of clauses 1 to 7 wherein the fibrous composition has a basis weight value of about 22 $g/m^2$.
11. The fibrous composition of any of clauses 1 to 7 wherein the fibrous composition has a basis weight value of about 25 $g/m^2$ to about 50 $g/m^2$.
12. The fibrous composition of any of clauses 1 to 7 wherein the fibrous composition has a basis weight value of about 25 $g/m^2$ to about 75 $g/m^2$.
13. The fibrous composition of any of clauses 1 to 7 wherein the fibrous composition has a basis weight value of about 50 $g/m^2$.
14. The fibrous composition of any of clauses 1 to 13 wherein the N-halamine is impregnated in the fibrous composition.
15. The fibrous composition of any of clauses 1 to 14 wherein the fibrous composition is selected from the group consisting of air filters, facial masks, surgical masks, wound dressings, gauze bandages, surgical scrubs, surgical gowns, surgical drapes, surgical caps, surgical booties, clothing, dental sponges, surgical sponges, incontinence products, diapers, medical towels, medical bedding, bed pads, dry wipes, and wet wipes.
16. The fibrous composition of any of clauses 1 to 13 wherein the N-halamine is suspended in the matrix of the fibrous composition.
17. The fibrous composition of any of clauses 1 to 16 wherein the N-halamine is present in a solvent upon application to the fibrous composition.
18. The fibrous composition of clause 17 wherein the solvent is water.
19. The fibrous composition of clause 17 wherein the solvent is an organic solvent.
20. The fibrous composition of clause 17 wherein the solvent is an alcohol.
21. The fibrous composition of clause 20 wherein the alcohol is ethyl alcohol.
22. The fibrous composition of clause 20 wherein the alcohol is isopropyl alcohol.
23. The fibrous composition of clause 17 wherein the solvent is a volatile solvent.
24. The fibrous composition of clause 23 wherein the volatile solvent is evaporated on the fibrous composition.
25. The fibrous composition of any of clauses 1 to 24 wherein the fibrous composition is capable of inactivation of one or more pathogenic microorganisms.
26. The fibrous composition of any of clauses 1 to 24 wherein the fibrous composition is capable of inactivation of one or more odor-causing microorganisms.
27. The fibrous composition of any of clauses 5 to 26 wherein the concentration of the 1-chloro-2,2,5,5-tetramethyl-4-imidazolidinone in the solvent is between about 0.002 to about 3.0 percent by weight.
28. The fibrous composition of any of clauses 5 to 26 wherein the concentration of the 1-chloro-2,2,5,5-tetramethyl-4-imidazolidinone in the solvent is between about 0.5 to about 1.5 percent by weight.
29. The fibrous composition of any of clauses 5 to 26 wherein the concentration of the 1-chloro-2,2,5,5-tetramethyl-4-imidazolidinone in the solvent is about 1.0 percent by weight.
30. A method of protecting a person from an infection, said method comprising the step of contacting the person with a fibrous composition comprising an N-halamine.
31. The method of clause 30 wherein the N-halamine is a soluble N-halamine.
32. The method of clause 30 wherein the N-halamine is a dispersible N-halamine.
33. The method of any one of clauses 30 to 32, wherein the N-halamine is selected from the group consisting of 1-chloro-2,2,5,5-tetramethyl-4-imidazolidinone, 3-chloro-4,4-dimethyl-2-oxazolidinone, 1,3-dichloro-2,2,5,5-tetramethyl-4-imidazolidinone, 1,3-dichloro-4,4,5,5-tetramethyl-2-imidazolidinone, tetrachloroglycoluril, and 1-chloro-2,2,6,6-tetramethyl-4-piperidinol.
34. The method of any one of clauses 30 to 32, wherein the N-halamine is 1-chloro-2,2,5,5-tetramethyl-4-imidazolidinone.
35. The method of any of clauses 30 to 34 wherein the person is a healthcare personnel.
36. The method of clause 35 wherein the healthcare personnel is in the proximity of a person inflicted with the infection.
37. The method of any of clauses 30 to 34 wherein the person is a patient.
38. The method of clause 37 wherein the infection is a nosocomial infection.
39. The method of any of clauses 30 to 34 wherein the person is in a public place.
40. The method of any of clauses 30 to 39 wherein the infection is a bacterial infection.
41. The method of clause 40 wherein the bacterial infection is caused by an airborne bacterium.
42. The method of clause 40 or clause 41 wherein the bacterial infection is caused by a pathogenic bacterium.
43. The method of any of clauses 40 to 42 wherein the bacterial infection is caused by an odor-causing bacterium.
44. The method of any of clauses 40 to 43 wherein the bacterial infection is caused by a Gram positive bacterium.
45. The method of clause 44 wherein the Gram positive bacterium is *Staphylococcus aureus*.
46. The method of any of clauses 40 to 43 wherein the bacterial infection is caused by a Gram negative bacterium.

47. The method of clause 46 wherein the Gram negative bacterium is *Escherichia coli*.

48. The method of clause 47 wherein the *Escherichia coli* is *E. coli*O157:H7.

49. The method of clause 46 wherein the Gram negative bacterium is *Pseudomonas aeruginosa*.

50. The method of any of clauses 30 to 39 wherein the infection is a viral infection.

51. The method of clause 50 wherein the viral infection is caused by an airborne virus.

52. The method of any of clauses 30 to 51 wherein the contact on the person with the fibrous composition is a dermatological contact.

53. The method of any of clauses 30 to 52 wherein the fibrous composition is a disposable fibrous composition.

54. The method of any of clauses 30 to 53 wherein the fibrous composition is a stable fibrous composition.

55. The method of any of clauses 30 to 54 wherein the fibrous composition has a basis weight value of about 15 $g/m^2$ to about 25 $g/m^2$.

56. The method of any of clauses 30 to 54 wherein the fibrous composition has a basis weight value of about 20 $g/m^2$ to about 50 $g/m^2$.

57. The method of any of clauses 30 to 54 wherein the fibrous composition has a basis weight value of about 22 $g/m^2$.

58. The method of any of clauses 30 to 54 wherein the fibrous composition has a basis weight value of about 25 $g/m^2$ to about 50 $g/m^2$.

59. The method of any of clauses 30 to 54 wherein the fibrous composition has a basis weight value of about 25 $g/m^2$ to about 75 $g/m^2$.

60. The method of any of clauses 30 to 54 wherein the fibrous composition has a basis weight value of about 50 $g/m^2$.

61. The method of any of clauses 30 to 60 wherein the N-halamine is impregnated in the fibrous composition.

62. The method of any of clauses 30 to 61 wherein the fibrous composition is selected from the group consisting of air filters, facial masks, surgical masks, wound dressings, gauze bandages, surgical scrubs, surgical gowns, surgical drapes, surgical caps, surgical booties, clothing, dental sponges, surgical sponges, incontinence products, diapers, medical towels, medical bedding, bed pads, dry wipes, and wet wipes.

63. The method of any of clauses 30 to 62 wherein the N-halamine is suspended in the matrix of the fibrous composition.

64. The method of any of clauses 30 to 63 wherein the N-halamine is present in a solvent upon application to the fibrous composition.

65. The method of clause 64 wherein the solvent is water.

66. The method of clause 64 wherein the solvent is an organic solvent.

67. The method of clause 64 wherein the solvent is an alcohol.

68. The method of clause 67 wherein the organic solvent is ethyl alcohol.

69. The method of clause 67 wherein the alcohol is isopropyl alcohol.

70. The method of clause 64 wherein the solvent is a volatile solvent.

71. The method of clause 70 wherein the volatile solvent is evaporated on the fibrous composition.

72. The method of any of clauses 34 to 71 wherein the concentration of the 1-chloro-2,2,5,5-tetramethyl-4-imidazolidinone in the solvent is between about 0.002 to about 3.0 percent by weight.

73. The method of any of clauses 34 to 71 wherein the concentration of the 1-chloro-2,2,5,5-tetramethyl-4-imidazolidinone in the solvent is between about 0.5 to about 1.5 percent by weight.

74. The method of any of clauses 34 to 71 wherein the concentration of the 1-chloro-2,2,5,5-tetramethyl-4-imidazolidinone in the solvent is about 1.0 percent by weight.

75. A method of producing a fibrous composition comprising an N-halamine, said method comprising the step of applying the N-halamine to the fibrous composition.

76. The method of clause 75 wherein the N-halamine is a soluble N-halamine.

77. The method of clause 75 wherein the N-halamine is a dispersible N-halamine.

78. The method of any one of clauses 75 to 77, wherein the N-halamine is selected from the group consisting of 1-chloro-2,2,5,5-tetramethyl-4-imidazolidinone, 3-chloro-4,4-dimethyl-2-oxazolidinone, 1,3-dichloro-2,2,5,5-tetramethyl-4-imidazolidinone, 1,3-dichloro-4,4,5,5-tetramethyl-2-imidazolidinone, tetrachloroglycoluril, and 1-chloro-2,2,6,6-tetramethyl-4-piperidinol.

79. The method of any one of clauses 75 to 77, wherein the N-halamine is 1-chloro-2,2,5,5-tetramethyl-4-imidazolidinone.

80. The method of any of clauses 75 to 79 wherein the application is performed via a pad-dry technique.

81. The method of any of clauses 75 to 80 wherein the step of applying comprises placing the soluble or dispersible N-halamine in a liquid to form a solution or dispersion.

82. The method of clause 81 wherein the liquid is a solvent, and wherein the solvent is water.

83. The method of clause 81 wherein the liquid is a solvent, and wherein the solvent is an organic solvent.

84. The method of clause 81 wherein the liquid is a solvent, and wherein the solvent is an alcohol.

85. The method of clause 84 wherein the alcohol is ethyl alcohol.

86. The method of clause 84 wherein the alcohol is isopropyl alcohol.

87. The method of clause 81 wherein the liquid is a solvent, and wherein the solvent is a volatile solvent.

88. The method of any of clauses 75 to 87 wherein the step of applying comprises soaking the fibrous composition in a solution.

89. The method of any of clauses 75 to 87 wherein the step of applying comprises spraying a solution on the fibrous composition.

90. The method of clause 88 or clause 89 wherein the solvent is evaporated from the fibrous composition.

91. The method of any of clauses 75 to 90 wherein the step of applying comprises padding the fibrous composition.

92. The method of any of clauses 75 to 91 wherein the step of applying comprises drying the fibrous composition.

93. The method of any of clauses 75 to 92 wherein the fibrous composition is a disposable fibrous composition.

94. The method of any of clauses 75 to 93 wherein the fibrous composition is a stable fibrous composition.

95. The method of any of clauses 75 to 94 wherein the fibrous composition has a basis weight value of about 15 $g/m^2$ to about 25 $g/m^2$.

96. The method of any of clauses 75 to 94 wherein the fibrous composition has a basis weight value of about 20 $g/m^2$ to about 50 $g/m^2$.

97. The method of any of clauses 75 to 94 wherein the fibrous composition has a basis weight value of about 22 g/m².

98. The method of any of clauses 75 to 94 wherein the fibrous composition has a basis weight value of about 25 g/m² to about 50 g/m².

99. The method of any of clauses 75 to 94 wherein the fibrous composition has a basis weight value of about 25 g/m² to about 75 g/m².

100. The method of any of clauses 75 to 94 wherein the fibrous composition has a basis weight value of about 50 g/m².

101. The method of any of clauses 75 to 100 wherein the N-halamine is impregnated in the fibrous composition.

102. The method of any of clauses 75 to 101 wherein the fibrous composition is selected from the group consisting of air filters, facial masks, surgical masks, wound dressings, gauze bandages, surgical scrubs, surgical gowns, surgical drapes, surgical caps, surgical booties, clothing, dental sponges, surgical sponges, incontinence products, diapers, medical towels, medical bedding, bed pads, dry wipes, and wet wipes.

103. The method of any of clauses 79 to 102 wherein the concentration of the 1-chloro-2,2,5,5-tetramethyl-4-imidazolidinone in the solvent is between about 0.002 to about 3.0 percent by weight.

104. The method of any of clauses 79 to 102 wherein the concentration of the 1-chloro-2,2,5,5-tetramethyl-4-imidazolidinone in the solvent is between about 0.5 to about 1.5 percent by weight.

105. The method of any of clauses 79 to 102 wherein the concentration of the 1-chloro-2,2,5,5-tetramethyl-4-imidazolidinone in the solvent is about 1.0 percent by weight.

Various embodiments of the invention are described herein as follows. In one embodiment described herein, a fibrous composition is provided. The fibrous composition comprises an N-halamine.

In another embodiment described herein, a method of protecting a person from an infection is provided. The method comprises the step of contacting the person with a fibrous composition comprising an N-halamine. In yet another embodiment described herein, a method of producing a fibrous composition comprising an N-halamine is provided. The method comprises the step of applying the N-halamine to the fibrous composition.

The present disclosure provides a fibrous composition. The fibrous composition comprises an N-halamine. As used herein, the term "fibrous composition" refers to any composition which has as a component at least one type of fiber. An N-halamine is a compound containing one or more nitrogen-halogen covalent bonds that is normally formed by the halogenation of imide, amide, or amine groups and includes compounds having the following general structure:

In various aspects described herein, the N-halamine is a soluble N-halamine. In other aspects described herein, the N-halamine is a dispersible N-halamine.

In some embodiments described herein, the N-halamine is selected from the group consisting of 1-chloro-2,2,5,5-tetramethyl-4-imidazolidinone, 3-chloro-4,4-dimethyl-2-oxazolidinone, 1,3-dichloro-2,2,5,5-tetramethyl-4-imidazolidinone, 1,3-dichloro-4,4,5,5-tetramethyl-2-imidazolidinone, tetrachloroglycoluril, and 1-chloro-2,2,6,6-tetramethyl-4-piperidinol. In one embodiment, the N-halamine is 3-chloro-4,4-dimethyl-2-oxazolidinone. In another embodiment, the N-halamine is 1,3-dichloro-2,2,5,5-tetramethyl-4-imidazolidinone. In yet another embodiment, the N-halamine is 1,3-dichloro-4,4,5,5-tetramethyl-2-imidazolidinone. In one embodiment, the N-halamine is tetrachloroglycoluril. In another embodiment, the N-halamine is 1-chloro-2,2,6,6-tetramethyl-4-piperidinol.

In various embodiments provided herein, the N-halamine is 1-chloro-2,2,5,5-tetramethyl-4-imidazolidinone ("compound I"). Compound I is a stable N-halamine both in aqueous solution and in the solid state as long as it is not exposed to direct sunlight or extensive UV radiation. At ambient temperature, the hydrolysis equilibrium constant of compound I to produce its precursor 2,2,5,5-tetramethyl-4-imidazolidinone and "free chlorine" (HOCl) is lower than $10^{-11}$. At low concentration in aqueous solution (e.g., 25 mg/L), long contact times (typically between 1-10 hours, dependent on pH) are required to obtain a 6-log reduction of *Staphylococcus aureus*. However, the necessary contact time to obtain such a reduction is considerably reduced when higher concentrations of compound I are used. Furthermore, compound I is inexpensive and may be prepared according to the procedures described in U.S. Pat. No. 5,057,612, U.S. Pat. No. 5,126,057, or Tsao et al. ("Novel N-halamine Disinfectant Compounds," *Biotechnol. Prog.*, 1991; 7:60), the disclosures of all which are incorporated herein in their entirety.

Compound I has the following chemical formula:

In various embodiments described herein, the fibrous composition is a disposable fibrous composition. As used herein, the term "disposable" includes compositions designed for single use and for multiple use. In other embodiments, the fibrous composition is a stable fibrous composition. As used herein, the term "stable fibrous composition" refers to a composition that is stable to loss of oxidative chlorine when it is stored in an appropriate environment (e.g., a dark environment or an environment substantially free of fluorescent light). For instance, a fibrous composition may be considered to be a stable fibrous composition when it maintains stability to loss of oxidative chlorine over a time period of 3 months, 6 months, 9 months, or longer.

In some embodiments described herein, the fibrous composition has a basis weight value of about 15 g/m² to about 25 g/m². As used herein, the term "basis weight" refers generally to the weight of the fabric that comprises the fibrous composition. In other embodiments, the fibrous composition has a basis weight value of about 20 g/m² to about 50 g/m². In yet other embodiments, the fibrous composition has a basis weight value of about 22 g/m². In some embodiments, the fibrous composition has a basis weight value of about 25 g/m² to about 50 g/m². In other embodiments, the fibrous composition has a basis weight value of about 25 g/m² to about 75 g/m². In yet other embodiments, the fibrous composition has a basis weight value of about 50 g/m².

In various embodiments described herein, the N-halamine is impregnated in the fibrous composition. In some embodiments provided herein, the fibrous composition is selected from the group consisting of air filters, facial masks, surgical masks, wound dressings, gauze bandages, surgical scrubs, surgical gowns, surgical drapes, surgical caps, surgical booties, clothing, dental sponges, surgical sponges, incontinence products, diapers, medical towels, medical bedding, bed pads, dry wipes, and wet wipes.

In some embodiments provided herein, the fibrous composition is an air filter. In other embodiments provided herein, the fibrous composition is a facial mask. In yet other embodiments provided herein, the fibrous composition is a surgical mask. In some embodiments provided herein, the fibrous composition is a wound dressing. In other embodiments provided herein, the fibrous composition is a gauze bandage. In yet other embodiments provided herein, the fibrous composition is a surgical scrub. In some embodiments provided herein, the fibrous composition is a surgical gown. In other embodiments provided herein, the fibrous composition is a surgical drape. In yet other embodiments provided herein, the fibrous composition is a surgical cap. In some embodiments provided herein, the fibrous composition is a pair of surgical booties. In other embodiments provided herein, the fibrous composition is clothing. In yet other embodiments provided herein, the fibrous composition is a dental sponge. In some embodiments provided herein, the fibrous composition is a surgical sponge. In other embodiments provided herein, the fibrous composition is an incontinence product. In yet other embodiments provided herein, the fibrous composition is a diaper. In some embodiments provided herein, the fibrous composition is a medical towel. In other embodiments provided herein, the fibrous composition is a medical bedding. In yet other embodiments provided herein, the fibrous composition is a bed pad. In some embodiments provided herein, the fibrous composition is a dry wipe. In other embodiments provided herein, the fibrous composition is a wet wipe.

In various embodiments provided herein, the N-halamine is suspended in the matrix of the fibrous composition. In certain embodiments described herein, the N-halamine is present in a solvent upon application to the fibrous composition. As used herein, the term "solvent" has its general meaning understood in the art, for instance a material that dissolves another substance while not changing its physical state.

In certain embodiments described herein, the solvent is water. In other embodiments described herein, the solvent is an organic solvent. In yet other embodiments described herein, the solvent is an alcohol. In certain embodiments described herein, the alcohol is ethyl alcohol. In other embodiments described herein, the alcohol is isopropyl alcohol. In yet other embodiments described herein, the solvent is a volatile solvent. In certain aspects, the volatile solvent is evaporated on the fibrous composition. Solvents capable of being used according to the present disclosure are known in the art or may readily be ascertained by a person of ordinary skill in the art.

In certain aspects provided herein, the fibrous composition is capable of inactivation of one or more pathogenic microorganisms. For example, the fibrous composition may be capable of inactivating a pathogenic bacterium, a pathogenic virus, or another type of pathogenic microorganism. In other aspects, the fibrous composition is capable of inactivation of one or more odor-causing microorganisms.

In some embodiments provided herein, the concentration of the 1-chloro-2,2,5,5-tetramethyl-4-imidazolidinone ("compound I") in the solvent is between about 0.002 to about 3.0 percent by weight. In other embodiments, the concentration of the 1-chloro-2,2,5,5-tetramethyl-4-imidazolidinone in the solvent is between about 0.5 to about 1.5 percent by weight. In yet other embodiments, the concentration of the 1-chloro-2,2,5,5-tetramethyl-4-imidazolidinone in the solvent is about 1.0 percent by weight.

The present disclosure also provides a method of protecting a person from an infection. The method comprises the step of contacting the person with a fibrous composition comprising an N-halamine. The previously described embodiments of the fibrous composition comprising an N-halamine are applicable to the methods of protecting a person from an infection described herein.

In certain aspects, the person to be protected by the method is a healthcare personnel. In various embodiments, the healthcare personnel is in the proximity of a person inflicted with the infection. For example, medical personnel in contact with infected patients are contemplated to be protected by the provided methods.

In other aspects, the person to be protected by the method is a patient. In various embodiments, the patient is to be protected from a nosocomial infection. For example, patients may be protected from nosocomial infections due to their contact with medical personnel. As used herein, the term "nosocomial infection" refers to an infection originating in a health care facility, such as a hospital.

In other aspects, the person to be protected by the method is in a public place. For example, persons may be general consumers in public places that utilize the fibrous compositions described herein for protection or preventative measures from infection-causing organisms that may be present in potentially contaminated environments. Persons in some parts of the world routinely wear face masks in public places due to the potential of biological outbreaks, and these persons are encompassed within the scope of persons to be protected by the methods described herein.

In various embodiments described herein, the infection is a bacterial infection. In some embodiments, the bacterial infection is caused by an airborne bacterium. In some embodiments, the bacterial infection is caused by a pathogenic bacterium. In some embodiments, the bacterial infection is caused by an odor-causing bacterium.

In various aspects, the bacterial infection is caused by a Gram positive bacterium. In some embodiments, the Gram positive bacterium is *Staphylococcus aureus*. In other aspects, the bacterial infection is caused by a Gram negative bacterium. In some embodiments, the Gram negative bacterium is *Escherichia coli*. In certain embodiments, the *Escherichia coli* is *E. coli* O157:H7. In other embodiments, the Gram negative bacterium is *Pseudomonas aeruginosa*.

In various aspects disclosed herein, the infection is a viral infection. In certain embodiments, the viral infection is caused by an airborne virus.

In certain aspects of the described method, the contact on the person with the fibrous composition is a dermatological contact. For example, a "dermatological contact" can include any contact of the infection-causing organism with anywhere on the person's skin or on a membranous outer covering of the person. In other aspects of the described method, the contact on the person with the fibrous composition is a non-dermatological contact. In yet other aspects of the described method, the contact on the person is an airborne contact.

Furthermore, the term "contact" means any direct or indirect contact of the fibrous composition with the person to be protected. For example, an indirect contact of a fibrous composition with a person occurs when a person wears a face mask including nonwoven fabric which is embedded between two layers of the face mask.

The present disclosure also provides a method of producing a fibrous composition comprising an N-halamine. The method comprises the step of applying the N-halamine to the fibrous composition. The previously described embodiments of the fibrous composition comprising an N-halamine are applicable to the methods of producing a fibrous composition described herein.

In certain aspects, the application is performed via a pad-dry technique.

In various embodiments described herein, the step of applying according to the described method comprises placing the soluble or dispersible N-halamine in a liquid to form a solution or a dispersion. In certain embodiments described herein, the liquid is a solvent. In certain embodiments described herein, the solvent is water. In other embodiments described herein, the solvent is an organic solvent. In yet other embodiments described herein, the solvent is an alcohol. In certain embodiments described herein, the alcohol is ethyl alcohol. In other embodiments described herein, the alcohol is isopropyl alcohol. In yet other embodiments described herein, the solvent is a volatile solvent. In certain aspects, the volatile solvent is evaporated on the fibrous composition. Solvents capable of being used according to the present disclosure are known in the art or may readily be ascertained by a person of ordinary skill in the art. In certain aspects, the step of applying comprises soaking the fibrous composition in a solution or a dispersion. In other aspects, the step of applying comprises spraying a solution or a dispersion on the fibrous composition. In various embodiments, the solvent is evaporated from the fibrous composition.

In various embodiments described herein, the step of applying comprises padding the fibrous composition. For example, the fibrous composition can be padded through a wringer such as a laboratory wringer. In other embodiments, the step of applying comprises drying the fibrous composition. For example, the fibrous composition can be air-dried at room temperature or any other desired temperature below about 50° C., or the fibrous composition can be dried by utilizing a drying aid such as a mechanical drier.

While the invention is susceptible to various modifications and alternative forms, specific embodiments are herein described in detail. It should be understood, however, that there is no intent to limit the invention to the particular forms described, but on the contrary, the intention is to cover all modifications, equivalents, and alternatives falling within the scope of the invention.

EXAMPLE 1

Production and Synthesis of N-halamine 1-chloro-2,2,5,5-tetramethyl-4-imidazolidinone In the instant example, production and synthesis of the exemplary N-halamine 1-chloro-2,2,5,5-tetramethyl-4-imidazolidinone (compound I) is provided.

The exemplary N-halamine of compound I can be purchased commercially from the HaloSource Corporation (Bothell, Wash., U.S.A.). Furthermore, the exemplary N-halamine, compound I, can be synthesized using methods known to those of skill in the art. Aqueous solutions of the un-halogenated amine precursor for the compound may be exposed to a dilute aqueous solution of household bleach (e.g., sodium hypochlorite) or sodium chlorite or by bubbling in chlorine gas to form the N-chloramine. For example, compound I has been prepared by using chlorine gas to react with an aqueous alkaline solution of the precursor amine (see Tsao, et al., "Novel N-halamine Disinfectant Compounds," *Biotechnol. Prog.*, 1991; 7:60 and Worley et al., U.S. Pat. No. 5,057,612, herein both incorporated by reference in their entirety).

The precursor 2,2,5,5-tetramethyl-4-imidazolidinone can be prepared according to the method outlined in Tsao or in Worley based upon oxidation of the corresponding thione with hydrogen peroxide in basic solution. The thione can be prepared by the method of Christian (see "4-imidazolidinethiones," *J. Org. Chem.*, 1957; 22:396), which entails reaction of sodium cyanide, ammonium chloride, ammonium sulfide, and acetone in aqueous solution. The oxidative chlorine content, and hence purity, of compound I can be measured using a standard iodometric/thiosulfate titration procedure. Compound I in its pure form contains 20.1 percent by weight oxidative chlorine. It has a solubility in water at 22° C. of 1930 mg/L. The weight percent of oxidative chlorine present under these saturated conditions at 22° C. for compound I is 0.0388. However, the compound is much more soluble in ethyl or isopropyl alcohol, such that a solution greater than 5000 mg/L oxidative chlorine can easily be obtained.

EXAMPLE 2

Preparation and Use of N-halamine-Containing Antimicrobial Facial Masks

In the instant example, the exemplary N-halamine 1-chloro-2,2,5,5-tetramethyl-4-imidazolidinone (compound I) is prepared and evaluated in antimicrobial facial mask embodiments.

Electrostatically charged polypropylene melt blown nonwoven fabrics were obtained from Hollingsworth & Vose Company (East Walpole, Mass., U.S.A.) with basis weights of 50 g/m$^2$ and 22 g/m$^2$, which are produced for use as substrates for N95 type respirator and surgical face mask applications, respectively. The polypropylene nonwoven substrate meets the U.S. government NIOSH and European EN 149 standards for N95 and surgical respirator applications. Millipore filters (0.45 µm pore size) were obtained from VWR Inc. (Radnor, Pa., U.S.A.). Clorox® brand (Clorox, Inc., Oakland, Calif., U.S.A.) household bleach was used for chlorination. Bacteria cultures of *Staphylococcus aureus* ATCC 6538 and *Escherichia coli* O157:H7 ATCC 43895 were obtained from American Type Culture Collection (Rockville, Md., U.S.A.), and Trypticase soy agar was obtained from Difco Laboratories (Detroit, Mich., U.S.A.). The effect of the applications on air permeability of the fabrics was tested on a Frazier Precision Instrument (Hagerstown, Md., U.S.A.) air permeability tester (using Meriam red oil), both on 22 g/m$^2$ and 50 g/m$^2$ polypropylene nonwovens, at 21° C. and 65% relative humidity. The pressure drop was adjusted to 0.5 inch of water. Air permeability was recorded in cubic feet of airflow per min per square foot (ft$^3$/min/ft$^2$).

Compound I (1-chloro-2,2,5,5-tetramethyl-imidazolindinone) at 1 wt %) was dissolved in ethyl alcohol solution at room temperature, and then 300 cm² pieces of polypropylene nonwoven fabrics were soaked in the solution for 10 minutes. The fabrics were then padded through a laboratory wringer (Birch Brothers Southern, Waxhaw, N.C., U.S.A.) at low pressure settings. This procedure was followed by drying the fabrics at room temperature for 24 hours. The control fabrics were untreated 22 g/m² and 50 g/m² polypropylene nonwovens. Ethyl alcohol solvent does not alter either compound I or polypropylene.

A modified iodometric/thiosulfate titration procedure was used to determine the active chlorine content on the fabrics impregnated with compound I (see, for example, Worley et al., "Novel N-halamine Siloxane Monomers and Polymers for Preparing Biocidal Coatings," *Surf Coat. Int.*, Part B, 2005; 88:93, herein incorporated by reference in its entirety). $Cl^+\%$ was calculated by the equation given below, where $Cl^+\%$ is the weight percent of the oxidative chlorine, N and V are $$Cl^+\ \% = \left(\frac{35.45 \times N \times V}{2 \times W}\right) \times 100$$

the normality (equiv/L) and volume (L) of the $Na_2S_2O_3$ (titrant), respectively, and W is the weight of the polypropylene fabric in grams.

Storage or shelf-life stability of the impregnated 22 g/m² fabrics was evaluated in the instant example. Fabric samples were stored in a cabinet (e.g., a dark environment) without exposure to fluorescent light and on the laboratory bench (e.g., under fluorescent light) at room temperature. The stability of the chlorine content over time was measured for 24 weeks. The stabilities of the fabrics impregnated with compound I with a basis weight of 22 g/m² were determined at 22° C. by measuring the amount of remaining chlorine on the fabrics by using the standard iodometric/thiosulfate titration procedure.

Two types of tests were conducted in order to determine the biocidal efficacy of the face mask embodiments. *Staphylococcus aureus* (*S. aureus*, ATCC 6538) was used as a Gram-positive bacterium and *Escherichia coli*(*E. coli* O157:H7, ATCC 43895) was used as a Gram-negative bacterium in order to challenge the treated (impregnated with compound I) and non-treated (control) fabrics.

In the first method, a "sandwich test" was used (see Worley et al., "Novel N-halamine Siloxane Monomers and Polymers for Preparing Biocidal Coatings," *Surf Coat. Int.*, Part B, 2005; 88:93). In this procedure, bacteria were suspended in 100 µM phosphate buffer (pH 7) to produce a suspension of known concentration of bacteria (colony forming units, CFU/mL). Then, an aliquot of 25 µL of this suspension was placed in the center of a 2.54 cm square swatch, and a second identical swatch was placed on top. Both swatches were covered by a sterile weight to ensure sufficient contact with the bacteria. After predetermined contact times, samples were quenched by 5.0 mL of sterile 0.02 N sodium thiosulfate solution to neutralize the oxidative chlorine and thus terminate the disinfection action. Samples were vortexed for 2 minutes, and then serial dilutions were prepared using pH 7, 100 µM phosphate buffer and plated on Trypticase soy agar plates. After incubating the plates at 37° C. for 24 hours, bacterial colonies were counted for the biocidal efficacy analysis. For each contact time a single fabric swatch sandwich was vortexed in a quenching solution to wash the bacteria into a suspension which was immediately plated into duplicate serial dilutions followed by incubation and counting the viable colonies of bacteria. All experiments were performed at least twice (on different days) using different bacterial inocula.

Figure 1:
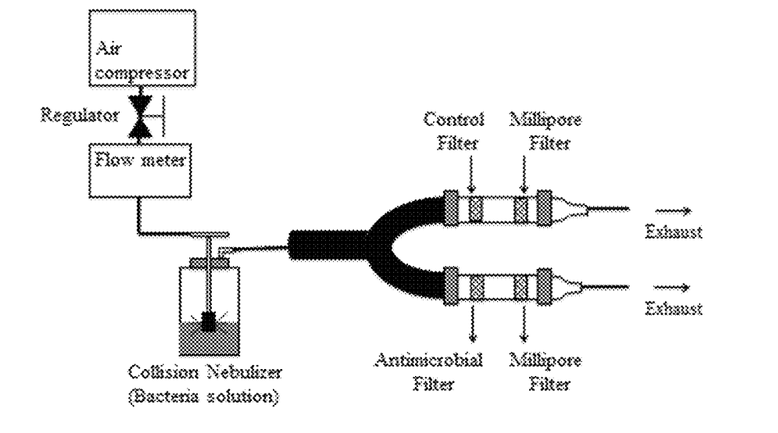
FIG. 1 shows the experimental setup for testing the exemplary N-halamine, 1-chloro-2,2,5,5-tetramethyl-4-imidazolidinone, in an antimicrobial air filter application against pathogenic bacteria in a flowing air stream.

The second procedure was based on ASTM Method F 2101.01 "Standard Test Methods for Evaluating the Bacterial Filtration Efficiency of Medical Face Mask Materials, Using a Biological Aerosol of *Staphylococcus aureus*," and a modified version of the method was applied. A bacteria suspension was prepared in 200 mL of 100 µM phosphate buffer (pH 7) to produce a suspension of known population (colony forming units, CFU/mL). First, small samples of two test fabrics (3.175 cm diameter, 7.91 cm²), one being impregnated with compound I and the other being a non-impregnated control, were clamped into a filter chamber under sterile conditions before challenging with aerosolized bacteria. *S. aureus* and *E. coli* O157:H7 bacteria, respectively, were aerosolized by using a one jet nebulizer through the chamber. A diagram of the experimental apparatus is shown in FIG. 1.

Aerosolized bacteria were introduced into the U-shaped aerosol chamber by using compressed laboratory air where the streaming air pressure was adjusted to 20 psi through a pressure regulator. Airflow was set to 259 mL/min by a flow meter and allowed to pass through the treated and non-treated test fabrics for 3 hours. Approximately 0.046 m³ of air contaminated with bacteria was aerosolized from the nebulizer, but only a fraction of the bacteria contacted the test fabrics due to the torturous path between the nebulizer and the chambers containing the test fabrics. After 3 hours of challenge, the aerosol flow was terminated, and the mask samples were retained in the test chamber for an additional 10 minutes.

Small porous (0.45 µm) sterilized Millipore filters were mounted downstream from the test fabrics. Any bioaerosols which penetrated through the mask samples were collected onto the Millipore filters in the chamber. After the additional 10 minute residence in the chamber, the samples were aseptically removed and transferred into 5.0 mL of sterile 0.02 N sodium thiosulfate solution to neutralize any chlorine and thus terminate the disinfection action. Similar to the previous analysis process, the mask samples were vortexed for 2 minutes, and then tenfold serial dilutions were prepared using pH 7, 100 µM phosphate buffer and plated on Trypticase soy agar plates. After incubating the plates at 37° C. for 24 hours, bacterial colonies were counted for the biocidal efficacy analysis. All experiments were performed in duplicate on different days.

The presence of compound I in the impregnated fabrics was confirmed by FTIR characterization. The analytical titration results for the fabrics showed the presence of oxidative chlorine bonded to compound I. Importantly, compound I was not chemically bonded to the polypropylene fibers and did not affect their structures; rather, compound I was adsorbed on the fibers and could not be removed mechanically, but only by solubilization with water.

Shelf life stability results are summarized in Table 1. Fabrics which were stored in dark environmental conditions retained their initial chlorine loadings, i.e. the fabrics showed no significant chlorine loss during a 6 month time period. The variation in the chlorine loadings shown in Table 1 can be attributed to different initial sample loadings due to inconsistencies in the filter sample materials. However, when the fabrics were exposed to fluorescent light, a rapid chlorine loss was observed. Almost all of the initial chlorine loading was lost within a 2 week time period, and the remaining chlorine was lost after 3 weeks of exposure. In order to provide antimicrobial activity, 0.04 wt % Cl+ loading was suggested to be sufficient. Fabrics can still show biocidal efficacy after 2 weeks of fluorescent light exposure. The chlorine loss from the fabrics was associated with the N—Cl bond photo dissociation. A filter material impregnated with compound I should be stored in opaque packaging in a real applications.

TABLE 1

Storage Stability of the Fabrics Impregnated with Compound I[a].

| Time (weeks) | Dark storage[b] | Fluorescent-light[b] |
|---|---|---|
| Initial | 0.36 | 0.40 |
| 2 | 0.37 | 0.05 |
| 3 | 0.40 | 0 |
| 5 | 0.37 | 0 |
| 8 | 0.40 | 0 |
| 12 | 0.42 | 0 |
| 24 | 0.41 | 0 |

[a]The error in the measured Cl+ loading was about ±0.01.
[b]Chlorine loadings are reported in wt % Cl+.

Compound I impregnation of the fabrics did not significantly influence the air permeability of the fabrics, as the air permeability of the treated 50 g/m$^2$ and 22 g/m$^2$ fabrics remained essentially the same as for the non-treated fabrics. It was recorded that the average air permeability of the impregnated higher weight basis fabrics (50 g/m$^2$) and the lower weight basis fabrics (22 g/m$^2$) were 28±0.5 ft$^3$/min/ft$^2$ and 52.5±1.5 ft$^3$/min/ft$^2$, respectively. This is due to the product development of the materials. Since 50 g/m$^2$ fabrics were designed to filter 95% of airborne particles, the pore sizes of the fabric were smaller than for the 22 g/m$^2$ fabric. In addition, the greater thickness (0.43 mm) of the 50 g/m$^2$ fabric could cause lower air flow permeability than for the thinner (0.16 mm) 22 g/m$^2$ fabric. The impregnated fabrics exhibited air permeability higher than most protective clothing materials currently in use and higher than for a previous antimicrobial polymer coated polypropylene (Cerkez, et al., "Antimicrobial Surface Coatings for Polypropylene Nonwoven Fabrics," *React. Funct. Polym.*, 2013; 73:1412) and most protective clothing materials currently studied (Lee et al., "Developing Protective Textile Materials as Barriers to Liquid Penetration using Melt-electrospinning," *J. Appl. Polym. Sci.*, 2006; 102:3430).

Antimicrobial efficacy of the mask materials was analyzed by the sandwich contact test method. The antimicrobial efficacies of the treated (impregnated with compound I) and non-treated (control) swatches were evaluated by challenging both types of fabrics against *S. aureus* and *E. coli* O157:H7 where the bacteria inoculum population was 1.80× 10$^6$ CFU and 1.27×10$^6$ CFU, respectively. In Table 2, antimicrobial results are summarized at different contact time intervals.

Both of the formulated test fabrics, with basis weights of 50 g/m$^2$ and 22 g/m$^2$, showed significant bacterial reduction against *S. aureus* and *E. coli* O157:H7 bacteria. The non-impregnated (control) samples exhibited much lower reductions even after 30 minutes of contact time. These reductions were due to adherence of live bacteria to the mask sample, not to inactivating bacteria. Both types of fabric showed complete 6 log inactivation against *E. coli* O157:H7 after 10 minutes of contact time. The fabrics exhibited a somewhat better inactivation rates against *S. aureus*.

Even though tested fabrics comprise the same N-halamine compound and oxidative chlorine loadings, the inactivation rate was different between the low and high basis-weight of fabrics against *S. aureus*. Lighter weight fabrics had a slower inactivation rate compared to heavier weight fabrics. The heavier fabrics showed 6.26 log reduction within 5 minutes of contact time, whereas lighter fabrics provided a 4.13 log reduction. Since heavier fabrics (50 g/m$^2$) held a higher number of chlorine atoms than the lighter weight (22 g/m$^2$) fabrics due to the greater surface areas provided by the thickness of fabric, inactivation of the bacteria was more rapid for the heavier fabrics. Although they possessed lower concentrations of chlorine atoms, the lighter weight fabrics were still very effective, as it required only 10 minutes to inactivate the *S. aureus* bacteria completely.

TABLE 2

Biocidal Efficacy Results of 1 wt % Compound I-Impregnated Polypropylene Nonwoven Face-Piece Material

| Samples | | Contact time (min) | Bacterial reduction (log) | |
|---|---|---|---|---|
| | | | *S. aureus*[a] | *E. coli*[b] |
| 22 g/m$^2$ | Control | 30 | 1.64 | 0.047 |
| | Compound I | 5 | 4.13 | 3.68 |
| | Cl+ % = 0.52 | 10 | 6.26 | 6.10 |
| | | 15 | 6.26 | 6.10 |
| | | 30 | 6.26 | 6.10 |
| 50 g/m$^2$ | Control | 30 | 1.69 | 0.023 |
| | Compound I | 5 | 6.26 | 3.80 |
| | Cl+ % = 0.52 | 10 | 6.26 | 6.10 |
| | | 15 | 6.26 | 6.10 |
| | | 30 | 6.26 | 6.10 |

[a]The inoculum for *S. aureus* bacteria was 1.80 × 10$^6$ CFU or 6.26 log per sample.
[b]The inoculum for *E. coli* O157:H7 bacteria was 1.27 × 10$^6$ CFU or 6.10 log per sample.

The treated (impregnated with compound I) and non-treated (control) samples of both types of fabrics were also tested against *S. aureus* and *E. coli* O157:H7 by an aerosol test. The results of 50 g/m$^2$ and 22 g/m$^2$ polypropylene samples are shown against *E. coli* O157:H7 and *S. aureus* bioaerosols in Tables 3 and 4, respectively. Both types of fabrics were remarkably effective against both types of aerosols. Untreated samples of both types of fabrics (50 g/m$^2$ and 22 g/m$^2$) were used as controls. For example, after 3 hours of aerosol nebulization, the average *E. coli* O157:H7 bacteria loading onto 50 g/m$^2$ and 22 g/m$^2$ control specimens from two different sets of experiments were 2.15×10$^3$ CFU/sample and 1.60×10$^3$ CFU/sample, respectively (see Table 3 and Table 4). The average viable *S. aureus* bacteria collected on the 50 g/m$^2$ and 22 g/m$^2$ control specimens were 6.08× 10$^4$ CFU/sample and 1.92×10$^5$ CFU/sample, respectively (see Table 3 and Table 4).

The experiments were performed on different days. Therefore, different bacterial solutions were used in each experiment even though the CFU concentrations of bacteria were prepared to be the same (1×10$^8$ CFU/mL). The slight difference of bacterial loading on control samples for each experiment was as expected for these types of challenging experiments. The total number of collected *E. coli* O157:H7 aerosol CFU was consistently less than the total number of the collected *S. aureus* aerosol CFU. This could possibly be attributed to the effect of the bacterial shapes and the aerodynamic sizes of *S. aureus* (spheres) versus *E. coli* (rods) in the nebulized air stream striking the walls of the tubing and adsorbing there. Also, in the instant example, no organisms survived to be caught by the Millipore filters for either the treated or the untreated fibers, although the organisms were not inactivated by the control fibers. Regardless, the fabrics impregnated with compound I exhibited significant reduction against *E. coli* O157:H7 and against *S. aureus* aerosols and inactivated the total concentrations of the aerosols collected on the fabrics.

When compared to current investigations on antimicrobial filter masks, the instant results present greater antimicrobial activity. Moreover, in this example, a Millipore type filter material was mounted behind the test fabrics in order to collect bioaerosols that could pass through the control and impregnated fabrics. No viable bacteria were observed on the Millipore filter material, which indicates that both types of nonwoven fabrics were effective in capturing all of the aerosolized bacteria and were effective in inactivating the total aerosolized number of the bacteria when impregnated with compound I. This suggests that N95 and surgical types of masks used in this example can prevent the penetration/bypass of the aerosol bacteria. Furthermore, in a real use scenario, compound I could be applied to an internal melt-blown layer which would not contact the skin of the user. Accordingly, there are no issues of biocompatibility or toxicity since compound I is not volatile (mp of 157° C.) and does not emit any chlorine gas (dissociation constant lower than $10^{-11}$). The filter masks would be disposable after a single use and could be stored in sealed opaque packages to prevent premature contact with moisture or light, thus preventing loss of compound I during long shelf-life storage.

In summary, facial masks impregnated with the exemplary N-halamine, compound I, are effective in prevention of the spread of aerosolized pathogens and thus would be effective in preventing the spread of infections. Furthermore, air filters, in general, impregnated with compound I should be effective in preventing the spread of diseases.

TABLE 3

Biocidal Efficacies of 50 g/m² Fabrics against *E. coli* O157:H7 and *S. aureus* Bioaerosols.

| Samples (50 g/m²) | Aerosol Exposure Time | Viable Bacteria Recovered (CFU/sample) | | | |
|---|---|---|---|---|---|
| | | *E. coli* (Exp 1) | *E. coli* (Exp 2) | *S. aureus* (Exp 3) | *S. aureus* (Exp 4) |
| Control | 3 h | 2.90 × 10³ | 1.40 × 10³ | 1.47 × 10⁴ | 1.07 × 10⁵ |
| Compound I Cl⁺ % = 0.47 | 3 h | 0 | 0 | 0 | 0 |
| Filter[a] | 3 h | 0 | 0 | 0 | 0 |
| Filter[b] | 3 h | 0 | 0 | 0 | 0 |

[a] The Millipore sterile filter material on control side of the chamber.
[b] The Millipore sterile filter material on compound I side of the chamber.

TABLE 4

Biocidal Efficacies of 22 g/m² Fabrics against *E. coli* O157:H7 and *S. aureus* Bioaerosols.

| Samples (22 g/m²) | Aerosol Exposure Time | Viable Bacteria Recovered (CFU/sample) | | | |
|---|---|---|---|---|---|
| | | *E. coli* (Exp 5) | *E. coli* (Exp 6) | *S. aureus* (Exp 7) | *S. aureus* (Exp 8) |
| Control | 3 h | 1.87 × 10³ | 1.33 × 10³ | 1.00 × 10⁴ | 3.73 × 10⁵ |
| Compound I Cl⁺ % = 0.47 | 3 h | 0 | 0 | 0 | 0 |

TABLE 4-continued

Biocidal Efficacies of 22 g/m² Fabrics against *E. coli* O157:H7 and *S. aureus* Bioaerosols.

| Samples (22 g/m²) | Aerosol Exposure Time | Viable Bacteria Recovered (CFU/sample) | | | |
|---|---|---|---|---|---|
| | | *E. coli* (Exp 5) | *E. coli* (Exp 6) | *S. aureus* (Exp 7) | *S. aureus* (Exp 8) |
| Filter[a] | 3 h | 0 | 0 | 0 | 0 |
| Filter[b] | 3 h | 0 | 0 | 0 | 0 |

[a] The Millipore sterile filter material on control side of the chamber.
[b] The Millipore sterile filter material on compound I side of the chamber.

EXAMPLE 3

Preparation and Use of N-halamine-Containing Antimicrobial Wound Dressings

In the instant example, the exemplary N-halamine 1-chloro-2,2,5,5-tetramethyl-4-imidazolidinone (compound I) is prepared and evaluated in antimicrobial wound dressing embodiments.

Compound I at a concentration of 1% by weight was dissolved in ethyl alcohol at room temperature. Non-stick gauze pads sized 20.3×7.6 cm (8×3 inch) obtained from Curad® were soaked in the solution for 10 minutes. The gauze pads were then passed through a laboratory wringer (Birch Brothers Southern, Waxhaw, N.C., U.S.A.) at low pressure settings. This procedure was followed by drying the samples at room temperature overnight. The titrated oxidative chlorine loading of the gauze pads was 0.47±0.01 wt %.

Gauze pads impregnated with compound I and non-impregnated sterile gauze pads (used as received as controls) were challenged with *Staphylococcus aureus* (*S. aureus*, ATCC 6538), *Escherichia coli*(*E. coli* O157:H7, ATCC 43895), and *Pseudomonas aeruginosa* (*P. aeruginosa*, ATCC 27853). The bacteria were suspended in 100 μM phosphate buffer (pH 7) to produce a suspension of known population (colony forming units, CFU/mL). Then, an aliquot of 25 μL of this suspension was placed in the center of a 2.54×2.54 cm² gauze swatch, and a second identical swatch was placed on top. Both swatches were covered by a sterile weight to ensure sufficient contact with the bacteria. After predetermined contact times, samples were quenched by 5.0 mL of sterile 0.02 N sodium thiosulfate solution to neutralize the oxidative chlorine and thus terminate the disinfection action. Samples were vortexed for 2 minutes, and then serial dilutions were prepared using pH 7, 100 μM phosphate buffer and plated on Trypticase soy agar plates. After the plates were incubated at 37° C. for 24 hours, viable bacterial colonies were counted for the biocidal efficacy analysis.

The results of the instant experiment are shown in Table 5.

TABLE 5

Biocidal Efficacies of Gauze Pads Impregnated and Non-Impregnated with Compound I against *S. aureus*, *E. coli* O157:H7 and *P. aeruginosa*.

| | | Bacterial Reduction (log) | | |
|---|---|---|---|---|
| Samples | Contact Time (min) | *S. aureus** | *E. coli* O157:H7 | *P. aeruginosa** |
| Control | 30 | 0.16 | 0.15 | 0.37 |
| Compound I | 1 | 3.07 | 5.86 | 6.12 |
| | 5 | 6.00 | 5.86 | 6.12 |
| | 10 | 6.00 | 5.86 | 6.12 |
| | 30 | 6.00 | 5.86 | 6.12 |

*The inoculum concentrations were 6.00, 5.86 and 6.12 logs for *S. aureus*, *E. coli* O157:H7, and *P. aeruginosa*, respectively. The chlorine loading on the samples impregnated with compound I was 0.47 ± 0.01 wt %.

As shown in Table 5, gauze samples impregnated with compound I inactivated about 6 log of *E. coli* O157:H7 and *P. aeruginosa* within 1 minute and showed a complete 6 log inactivation of *S. aureus* within the interval of 1 to 5 minutes of contact time. It can be concluded that impregnation of wound dressings with compound I has great potential for controlling infections in wounds.

EXAMPLE 4

Preparation and Use of N-halamine-Containing Antimicrobial Wipes

In the instant example, the exemplary N-halamine 1-chloro-2,2,5,5-tetramethyl-4-imidazolidinone (compound I) is prepared and evaluated in antimicrobial wipe embodiments. Two types of antimicrobial evaluations were performed in the instant example. The first test was designed to evaluate the potential of wet wipes impregnated with compound I to inactivate bacteria upon direct contact. The second test was designed to evaluate the potential of compound I to prevent the growth of bacteria when compound I was deposited on a surface by a wet wipe.

In the first test, CVS brand commercial wet wipes were first dried at 45° C. for 1 hour before impregnation with solutions of compound I. Different concentrations (wt %) of compound I were prepared in ethyl alcohol, and the wipes were soaked in the solutions for 5 minutes. After soaking in the solutions, each wipe was mounted between two filter papers, and a weight of 290 grams was placed uniformly over the stack. At the end of a 30 second period, the wet wipes were placed in closed vials to prevent further loss of solvent. Table 6 shows the wet weight gains (wt %) and oxidative chlorine loading measured by iodometric/thiosulfate titration of the wipes impregnated with different concentrations of compound I. The chlorine loading increased linearly with an increase of compound I concentration in ethyl alcohol solution.

TABLE 6

Chlorine Loadings (Cl$^+$ wt %) and Weight Gains (wt %) of the Wipes in Different Concentrations of Compound I Solutions.

| Concentration of Compound I in Ethyl Alcohol (wt %) | Wet Weight Gain (wt %) | *Chlorine Loading (Cl$^+$ wt %) | |
|---|---|---|---|
| | | by wet weight | by dry weight |
| 1.5 | 79 | 0.24 | 1.14 |
| 1.0 | 76 | 0.16 | 0.66 |
| 0.5 | 80 | 0.08 | 0.40 |
| 0.25 | 75 | 0.04 | 0.16 |

*The error in the measured Cl$^+$ weight percentage values was ±0.01.

For antibacterial testing, CVS brand commercial wipes were used as received as controls and wipes impregnated with compound I at a concentration of 1.0 wt % in ethyl alcohol were prepared as described above. The impregnated and non-impregnated wipes were challenged with *Staphylococcus aureus* (*S. aureus*, ATCC 6538 and *Escherichia coli* (*E. coli* O157:H7, ATCC 43895). Bacteria were suspended in 100 μM phosphate buffer (pH 7) to produce a suspension of known population (colony forming units, CFU/mL). Then, an aliquot of 25 μL of this suspension was placed in the center of a 4 layers of 2.54×2.54 cm swatches, and a second identical 4 layers of swatches were placed on top. Both swatches were covered by a sterile weight to ensure sufficient contact with the bacteria. After predetermined contact times, samples were quenched by 5.0 mL of sterile 0.02 N sodium thiosulfate solution to neutralize the oxidative chlorine and thus terminate the disinfection action. Samples were vortexed for 2 minutes, and then serial dilutions were prepared using pH 7, 100 μM phosphate buffer and plated on Trypticase soy agar plates. After the plates were incubated at 37° C. for 24 hours, viable bacterial colonies were counted for the biocidal efficacy analysis.

Biocidal reduction of the wet wipes impregnated with compound I and the CVS brand commercial wipes against *S. aureus* and *E. coli* O157:H7 are shown in Table 7. The samples impregnated with compound I inactivated 6.5 logs of *E. coli* O157:H7 and 6.35 logs of *S. aureus* after only 1 minute of contact time. The CVS brand commercial wipes did not show a significant biocidal reduction of *S. aureus* at a contact time of 1 minute and only 3.22 logs after 10 minutes. However, the wipes were able to show a complete 6.5 log reduction of *E. coli* O157:H7 after 5 minutes of contact. The alcohol content in the commercial wipes (about 76 wt %) can explain the log reductions since alcohol itself can inactivate bacteria to a certain extent. The presence of compound I in the wipes undoubtedly enhances their antimicrobial efficacy.

TABLE 7

Biocidal Efficacies CVS Brand Commercial Wipes against *S. aureus* and *E. coli* O157:H7 with and without Impregnated Compound I.

| | | Bacterial Reduction (logs) | |
|---|---|---|---|
| Samples | Contact Time (min) | *S. aureus*[a] | *E. coli* O157:H7[a] |
| CVS brand wipes | 1 | 0.48 | 1.52 |
| | 2 | 0.51 | 1.72 |
| | 3 | 0.92 | 2.00 |
| | 5 | 1.04 | 6.50 |
| | 10 | 3.22 | 6.50 |

TABLE 7-continued

Biocidal Efficacies CVS Brand Commercial Wipes against *S. aureus* and *E. coli* O157:H7 with and without Impregnated Compound I.

| Samples | Contact Time (min) | Bacterial Reduction (logs) | |
|---|---|---|---|
| | | *S. aureus*[a] | *E. coli* O157:H7[a] |
| Compound I Impregnated wipes[b] | 1 | 6.35 | 6.50 |
| | 2 | 6.35 | 6.50 |
| | 3 | 6.35 | 6.50 |
| | 5 | 6.35 | 6.50 |
| | 10 | 6.35 | 6.50 |

[a]The inoculum concentrations were 6.35, and 6.50 for *S. aureus*, and *E. coli* O157:H7, respectively.
[b]The oxidative chlorine loading on samples impregnated with compound I was 0.66 ± 0.01 wt %.

In the second test, CVS brand commercial multi-surface wipes (not claimed to be antimicrobial) were first dried at 45° C. for 1 hour before impregnating with compound I. In particular, compound I was dissolved in ethyl alcohol at a concentration of 1.0 wt %, and the wipes were soaked in the solution for 5 minutes. CVS brand commercial multi-surface wipes soaked in ethyl alcohol were employed as controls. After soaking in the ethyl alcohol solutions, all of the wet wipes were mounted between two filter papers, and a weight of 290 grams was placed over the wipes. At the end of a 30 second period, the prepared wet wipes were transferred to closed vials to prevent the loss of further solvent. The oxidative chlorine loading of the wipes impregnated with compound I was 0.69±0.01 wt %.

The wipes impregnated with compound I and the control wipes were used to wipe 2.54×2.54 cm cut formica surfaces. In order to mimic the wiping process on surfaces, the wipes were held by sterile tweezers. A constant wiping application process was applied onto the formica pieces with the treated wipes for 30 seconds in order to ensure that each formica piece was fully coated. The process was repeated for wipes that were soaked in ethyl alcohol as a control experiment. A second control of the formica surfaces was used in which no wiping process was applied onto the surfaces prior to antimicrobial testing. After the evaporation of the volatile solvent, the formica sample surfaces were dry. The formica sample surfaces wiped with wipes impregnated with compound I contained a thin film of the compound.

The formica samples were then challenged with *Staphylococcus aureus* (*S. aureus*, ATCC 6538) and *Escherichia coli*(*E. coli* O157:H7, ATCC 43895) at different contact times in a "sandwich" test. Bacteria were suspended in 100 μM phosphate buffer (pH 7) to produce a suspension of known population (colony forming units, CFU/mL). Then, the formica surface was challenged with an aliquot of 25 μL of this suspension, and a second identical formica piece was placed on top. Both formica pieces were covered by a sterile weight to ensure sufficient contact with the bacteria. After predetermined contact times, samples were quenched by 5.0 mL of sterile 0.02 N sodium thiosulfate solution to neutralize the oxidative chlorine and thus terminate the disinfection action. Samples were vortexed for 2 minutes, and then serial dilutions were prepared using pH 7, 100 μM phosphate buffer and plated on Trypticase soy agar plates. After the plates were incubated at 37° C. for 24 hours, viable bacterial colonies were counted for the biocidal efficacy analysis. The results are shown in Table 8.

TABLE 8

Biocidal Efficacy of a Surface that is Challenged with Bacteria after Wiping the Surface with Wipes Impregnated with Compound I.

| Samples | Contact Time (min) | Bacterial Reduction (log) | |
|---|---|---|---|
| | | *S. aureus** | *E. coli* O157:H7* |
| Control[a] | 1 | 1.21 | 0.01 |
| | 5 | 1.27 | 0.05 |
| | 30 | 1.38 | 0.01 |
| | 60 | 1.66 | 0.09 |
| Control[b] | 1 | 1.13 | 0.03 |
| | 5 | 1.27 | 0.03 |
| | 30 | 1.48 | 0.07 |
| | 60 | 1.52 | 0.11 |
| Surface coated with Compound I[c] | 1 | 3.57 | 0.09 |
| | 5 | 6.00 | 0.16 |
| | 30 | 6.00 | 6.24 |
| | 60 | 6.00 | 6.24 |

[a]Control surfaces were not wiped with ethyl alcohol.
[b]Control surfaces were wiped with samples soaked in 100% ethyl alcohol and allowed to dry.
[c]Tested surfaces were wiped with samples impregnated with compound I and allowed to dry. The oxidative chlorine loading of the wipes impregnated with compound I was 0.69 ± 0.01 wt %.
*The inoculum concentrations were 6.00 and 6.24 logs for *S. aureus*, and *E. coli* O157:H7, respectively.

It can be concluded from the data in Table 8 that the applied film of compound I on a surface will prevent the growth of bacteria on the surface.

What is claimed is:

1. A composition comprising 1-chloro-2,2,5,5-tetramethyl-4-imidazolidinone and a fibrous composition,
   wherein the composition is a dried composition, and
   wherein the 1-chloro-2,2,5,5-tetramethyl-4-imidazolidinone is adsorbed on the fibrous composition, wherein the 1-chloro-2,2,5,5-tetramethyl-4-imidazolidinone is present in a solution consisting essentially of an alcohol-based solvent upon application to the fibrous composition.

2. The composition of claim 1 wherein the composition is a disposable composition.

3. The composition of claim 1 wherein the 1-chloro-2,2,5,5-tetramethyl-4-imidazolidinone is impregnated in the fibrous composition.

4. The composition of claim 1 wherein the fibrous composition is selected from the group consisting of air filters, facial masks, surgical masks, wound dressings, gauze bandages, surgical scrubs, surgical gowns, surgical drapes, surgical caps, surgical booties, clothing, dental sponges, surgical sponges, incontinence products, diapers, medical towels, medical bedding, bed pads, and dry wipes.

5. The fibrous composition of claim 1 wherein the 1-chloro-2,2,5,5-tetramethyl-4-imidazolidinone is suspended in the matrix of the fibrous composition.

6. The composition of claim 1 wherein the alcohol is ethanol.

7. The composition of claim 1 wherein the solvent is a volatile solvent.

8. The composition of claim 7 wherein the volatile solvent is evaporated on the fibrous composition.

9. The composition of claim 1, wherein the 1-chloro-2,2,5,5-tetramethyl-4-imidazolidinone is in a solid state.

10. The composition of claim 1, wherein the 1-chloro-2,2,5,5-tetramethyl-4-imidazolidinone is not removable mechanically from the dried fibrous composition.

11. The composition of claim 2, wherein the 1-chloro-2,2,5,5-tetramethyl-4-imidazolidinone is in a solid state.

12. The composition of claim 3, wherein the 1-chloro-2,2,5,5-tetramethyl-4-imidazolidinone is in a solid state.

13. The composition of claim 8, wherein the 1-chloro-2,2,5,5-tetramethyl-4-imidazolidinone is in a solid state.

14. A fibrous composition comprising 1-chloro-2,2,5,5-tetramethyl-4-imidazolidinone and a fibrous composition, wherein the fibrous composition is formed according to a process of
   a) dissolving 1-chloro-2,2,5,5-tetramethyl-4-imidazolidinone in a solution consisting essentially of an alcohol-based solvent;
   b) applying the solution of step a) to the fibrous composition;
   c) drying the fibrous composition of step b) to provide a dried fibrous composition, wherein the 1-chloro-2,2,5,5-tetramethyl-4-imidazolidinone is adsorbed on the fibrous composition.

* * * * *

UNITED STATES PATENT AND TRADEMARK OFFICE
CERTIFICATE OF CORRECTION

PATENT NO. : 10,178,866 B2
APPLICATION NO. : 14/875334
DATED : January 15, 2019
INVENTOR(S) : Worley et al.

Page 1 of 1

It is certified that error appears in the above-identified patent and that said Letters Patent is hereby corrected as shown below:

In the Claims

In Claim 5, Column 22, Line 50, please delete the word "fibrous."

In Claim 14, Column 23, Line 3, please delete the word "fibrous."

Signed and Sealed this
Sixteenth Day of April, 2019

Andrei Iancu
*Director of the United States Patent and Trademark Office*